(12) United States Patent
Shah et al.

(10) Patent No.: US 11,077,860 B2
(45) Date of Patent: Aug. 3, 2021

(54) EMBEDDED IN-VEHICLE PLATFORM FOR PROVIDING IMMERSIVE USER EXPERIENCES

(71) Applicant: Ford Global Technologies, LLC, Dearborn, MI (US)

(72) Inventors: Ayush Shah, Belleville, MI (US); Jeffrey Yeung, Canton, MI (US); Harald C. Martinez, Northville, MI (US); Oleg Gusikhin, Commerce Township, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 333 days.

(21) Appl. No.: 16/295,959

(22) Filed: Mar. 7, 2019

(65) Prior Publication Data
US 2020/0283005 A1 Sep. 10, 2020

(51) Int. Cl.
*B60W 50/00* (2006.01)
*B60H 3/00* (2006.01)
(Continued)

(52) U.S. Cl.
CPC ....... *B60W 50/0098* (2013.01); *A61B 5/0205* (2013.01); *A61B 5/6893* (2013.01); *A61M 21/02* (2013.01); *B60H 1/00964* (2013.01); *B60H 3/0035* (2013.01); *B60Q 3/80* (2017.02); *B60W 50/14* (2013.01); *G06Q 30/0601* (2013.01); *A61B 5/02438* (2013.01); *A61B 5/165* (2013.01); *A61B 2503/12* (2013.01); *A61M 2021/0016* (2013.01); *A61M 2021/0027* (2013.01); *A61M 2021/0044* (2013.01); *B60W 2540/22* (2013.01); *B60W 2710/30* (2013.01)

(58) Field of Classification Search
CPC ..... B60W 50/0098; B60W 50/14; B60Q 3/80; A61B 5/0205; A61B 5/6893; A61M 21/02; B60H 1/00964; B60H 3/0035; G06Q 30/0601
See application file for complete search history.

(56) References Cited

U.S. PATENT DOCUMENTS 9,162,574 B2    10/2015  Kolodziej
9,384,661 B1 *   7/2016  DeLuca ............ G01C 21/3617
(Continued)

OTHER PUBLICATIONS

Kelson, K., "Mood is an Important Factor in Safe Driving," Inhalio, Sep. 21, 2017 (5 pages).
(Continued)

*Primary Examiner* — Hussein Elchanti
(74) *Attorney, Agent, or Firm* — Michael Spenner; Eversheds Sutherland (US) LLP

(57) ABSTRACT

Systems and methods are disclosed for an embedded in-vehicle platform that provides immersive user experiences. An example method includes obtaining, by a vehicle controller of a vehicle, a preference profile for a user; loading the preference profile by the vehicle controller; determining a shopping experience of the user occurring on a vehicle shopping platform within the vehicle; determining an ambience profile of a merchant identified in the shopping experience; and controlling, by the vehicle controller, an in-vehicle ambience within the vehicle based on the ambience profile and the preference profile.

20 Claims, 4 Drawing Sheets

(51) Int. Cl.
| | |
|---|---|
| *B60Q 3/80* | (2017.01) |
| *B60W 50/14* | (2020.01) |
| *B60H 1/00* | (2006.01) |
| *A61B 5/0205* | (2006.01) |
| *A61B 5/00* | (2006.01) |
| *A61M 21/02* | (2006.01) |
| *G06Q 30/06* | (2012.01) |
| *A61M 21/00* | (2006.01) |
| *A61B 5/024* | (2006.01) |
| *A61B 5/16* | (2006.01) |

(56) References Cited

U.S. PATENT DOCUMENTS

2006/0235753 A1* 10/2006 Kameyama ............ B60Q 1/143
  705/15
2007/0124027 A1*  5/2007 Betzitza ................ B60W 40/02
  701/1
2008/0147319 A1*  6/2008 Cubillo .................. G01C 21/32
  701/431
2010/0110105 A1*  5/2010 Kinnunen .......... G01C 21/3664
  345/629
2014/0277888 A1*  9/2014 Dastoor .................... B60L 3/12
  701/22
2016/0019434 A1*  1/2016 Caldwell ............. G06K 9/4671
  345/474
2016/0089954 A1*  3/2016 Rojas Villanueva ........................
  B60H 1/00742
  701/36
2016/0154538 A1*  6/2016 Wang .................... G06F 3/0488
  715/771
2016/0195856 A1     7/2016 Spero
2017/0176198 A1*  6/2017 Tatourian ........... G06K 9/00845
2018/0126938 A1*  5/2018 Cordova ................ G08G 1/0112
2018/0240554 A1*  8/2018 Vasgaard ........... A61B 5/02055
2019/0049261 A1*  2/2019 Colby ................ G01C 21/3484

OTHER PUBLICATIONS

Michon, et al., "Mall atmospherics: the interaction effects of the mall environment on shopping behavior," Journal of Business Research, 58 (2005) 576-583.

Shanly, C., "Xevo Delivers Major Merchant Brands to Gene," Xevo, Dec. 5, 2017 (3 pages).

* cited by examiner

EMBEDDED IN-VEHICLE PLATFORM FOR PROVIDING IMMERSIVE USER EXPERIENCES

TECHNICAL FIELD

The present disclosure relates to systems and methods that provide a multi-sensory, in-vehicle experience. Some embodiments include devices or apparatuses embedded or integrated into vehicles that provide enhanced and immersive user experiences.

BACKGROUND

Currently, in-vehicle commercial experiences are limited to online shopping through mobile devices or human machine interfaces. For example, a user can purchase services or goods over his/her mobile device or through laptop devices. Concurrently, the use of autonomous or automated vehicles (AVs), as well as ride-sharing or ride-hailing services is increasing steadily. During trips, passengers can listen to their favorite music or watch movies, but other in-vehicle activities are difficult. Moreover, it is difficult within an in-vehicle experience to encourage passengers to purchase items or services.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
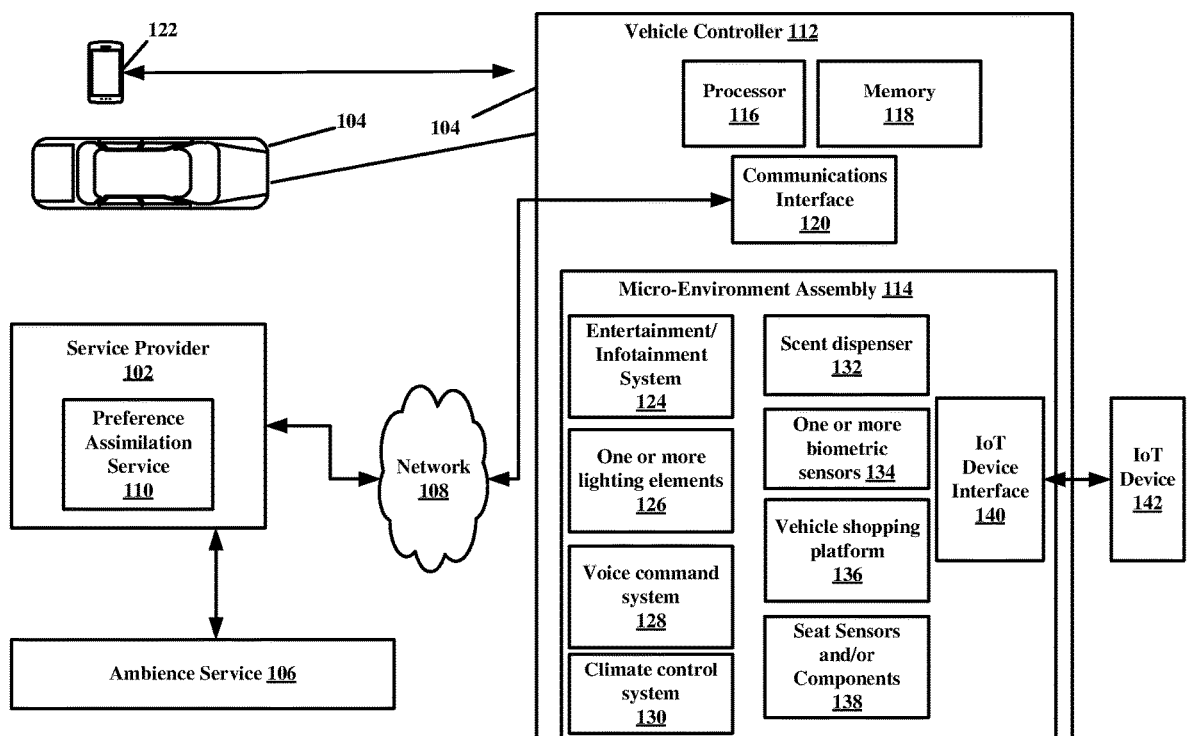
FIG. 1 depicts an illustrative architecture in which techniques and structures for providing the systems and methods disclosed herein may be implemented.

In some embodiments, systems and methods disclosed herein include embedded in-vehicle platforms for providing immersive user experiences. For example, a vehicle such as an AV or a non-autonomous vehicle can be configured to provide an immersive experience for a rider within the vehicle. In general, the vehicle can be configured to provide multi-sensory experiences involving combinations of visual, auditory, and olfactory elements.

Generally, the present disclosure allows for the use of odor, scent, and other vehicle ambience to increase passengers' confidence for performing shopping tasks. It will be understood that ambient odor acts as a moderating factor while a consumer is shopping. Such an ambient odor positively affects the consumer to entice the individual into buying a product or service.

Ambient scent can be used to control human behavior, mood, and emotions. Buying a specific item can depend upon the atmosphere or ambient environment near the consumer during a shopping experience. Positive environments can also be created by using ambient noise, soft music, ambient scent, and voice assist—just to name a few. In one example use case, a user is shopping for shoes in-vehicle during a ride-sharing trip. The user could be shopping in the vehicle using a vehicle tablet/computer to search for the retailer and item. Once the user selects a specific retailer, the vehicle can set an ambient environment to make the passenger feel as if he/she is shopping in a store. Further, ambient aromas can trigger the passenger to buy a specific item. In some embodiments, the ambient aroma dispensed can be different for each person. In this solution, the systems and methods can be configured to gather data about the user and store the same in a user profile (e.g., preference profile). Other ambient elements can also be tailored to known user preferences. This data can be used as input into a machine learning model or service that can be used to learn optimized ambient setting(s)/configuration(s) for each user and user profile.

According to some embodiments, a vehicle is provided with a micro-environment assembly that comprises a number of sub-assemblies or components that collectively provide the visual, auditory, and olfactory elements. In some embodiments, the micro-environment assembly is controlled using either or both of a preference profile and an ambience profile. Generally, a preference profile is a collection of data including subjective preferences or data regarding a user. This data can include, for example, demographic data of the user, calendar entries, contacts, purchasing and browsing histories, or more specific preference data gathered from user interactions with the vehicle such as climate control settings. In some embodiments, the data can include user preferences gathered from a user's interaction with a vehicle shopping platform within the vehicle. The vehicle shopping platform could include any device within the vehicle that the user utilizes to browse the Internet, or an application.

According to some embodiments, the vehicle can include various biometric sensors that capture biometric feedback of the user. This biometric feedback can be used to infer or determine mood, heart rate, or comfort level of the user. The biometric data is useful when correlated to a shopping experience of a user when inside the vehicle. Merchants can gather valuable information about users and their respective responses to ambient conditions and/or the shopping experience.

Advantageously, the systems and methods disclosed herein can be used to enhance an in-vehicle user shopping experience. Retailers or merchants can increase brand recognition through ambience profiling, allowing for individualized selections of aroma, lights, climate control, and the like. In some embodiments, the merchants can use the voice command system of a vehicle to engage in chats with a user and create a positive shopping environment. These and other aspects and advantages of the present disclosure are described in greater detail herein with reference to the collective drawings.

Illustrative Architecture

Turning now to the drawings, FIG. 1 depicts an illustrative architecture 100 in which techniques and structures of the present disclosure may be implemented. The illustrative architecture 100 may include a service provider 102 comprising service provider computers, a vehicle 104, an ambience service 106 comprising ambience service computers, and a network 108. The network 108 may include any one or a combination of multiple different types of networks, such as cable networks, the Internet, wireless networks, and other private and/or public networks. In some instances, the network 108 may include cellular, Wi-Fi, or Wi-Fi direct.

According to some embodiments, the service provider 102 is configured to maintain preference profiles and accounts for users who ride in vehicles configured to provide the immersive shopping experiences of the present disclosure. In some embodiments, the service provider 102 comprises a preference assimilation service 110 comprising preference assimilation service computers that implements aspects of machine learning in order to create preference models for users based on user behaviors and feedback, as will be discussed in greater detail infra. The service provider 102 can be implemented in a cloud in some embodiments.

The service provider 102 can also be configured to retrieve ambience profiles from the ambience service 106 and deliver the same to the vehicle 104. Broadly, an ambience profile includes a collection of parameters or configurations that can be implemented at the vehicle level to alter an ambience within the vehicle 104. The ambience profile allows a merchant to tailor the ambience within a vehicle to produce a desired user experience. In some embodiments, the desired user experience is one that entices the user into purchasing a good or service. For example, if the user is shopping for leather goods, the ambience profile could indicate that a leather scent should be dispensed within the vehicle. Other ambience settings could be included in the ambience profile such as dimmed lights and a temperature setting of a specific degree. It will be understood that this is merely an example of an ambience profile and that other parameters or configurations can be used.

In sum, the service provider 102 can provide the vehicle 104 both preference and ambience profiles. When used in combination, the preference and ambience profiles can result in the creation of a unique experience where the ambience within the vehicle is tailored to the preferences of the user while still enhancing the shopping experience of the user. The service provider 102 is also configured to collect user feedback and track user behaviors during an in-vehicle shopping experience in order to improve the preference and/or ambience profiles.

The vehicle 104 generally comprises a vehicle controller 112 and a micro-environment assembly 114. Generally described, the vehicle controller 112 comprises a processor 116 and a memory 118. The memory 118 stores instructions that can be executed by the processor 116 to perform various functions or operations disclosed herein. In general, the processor 116 can execute the instructions stored in the memory 118 to provide immersive shopping experiences in accordance with the present disclosure. This may occur through the loading and execution of personal and/or ambience profiles by the vehicle controller 112 to control the operations of the micro-environment assembly 114 (and constituent parts thereof) to create a customized ambience or environment within the vehicle 104. The vehicle controller 112 can also comprise a communications interface 120 that allows the vehicle controller 112 to communicate with the service provider 102 over the network 108. Also, the vehicle controller 112 can communicate with a mobile device or wearable 122 of a user within the vehicle. This allows the vehicle controller 112 to monitor shopping experiences on the mobile device or wearable 122 of the user, if such permissions are granted by the user. In some embodiments, the mobile device or wearable 122 can utilize a hotspot or other similar wireless connection or functionality provided through the vehicle controller 112 to access the Internet. The vehicle controller 112 can monitor network usage of this wireless connection. In one embodiment, the monitoring can include identifying Internet Protocol (IP) or domain names accessed by a browser on the mobile device or wearable 122. This data allows the vehicle controller 112 (or in some instances the service provider 102) to determine a merchant associated with a shopping experience of the user. The service provider 102 can retrieve an ambience profile for that specific merchant from the ambience service 106.

In some embodiments, the service provider 102 can also obtain a preference profile for the user and provide this preference profile along with the ambience profile to the vehicle controller 112. Once received, the vehicle controller 112 can load the ambience profile and/or the preference profile for the user. As noted above, the ambience profile and/or the preference profile are applied to create a unique and immersive shopping experience for the user.

In general, the micro-environment assembly 114 can include any one or more of an entertainment or infotainment system 124, one or more lighting elements 126, a voice command system 128, a climate control system 130, a scent dispenser 132, and one or more biometric sensors 134. Each of these subsystems is discussed in greater detail in the following paragraphs.

The entertainment or infotainment system 124 is configured to provide, for example, visual and/or auditory output for the user such as music, videos, or other media. In accordance with the present disclosure, the ambience profile could include music or other media that is selected by a merchant. In one example, if the merchant has a jingle or other media, the merchant can specify this media in the ambience profile. Another example could include a song for a particular product or service campaign. The ambience profile can also specify that music or media could also be selected based on the preference profile.

The one or more lighting elements 126 include any lighting devices that are located within the cabin of the vehicle 104. Some of these lighting elements 126 have selectable luminance and/or hue. Thus, the vehicle controller 112 can selectively alter or change the luminance and/or hue of the one or more lights in accordance with at least one of the ambience profile or the preference profile. In one example use case, the merchant can specify in an ambience profile that the lights in the cabin of the vehicle should be dimmed. This could be advantageous when the ambience profile specifies that a video is played on a display of the entertainment or infotainment system 124. A hue of the one or more lighting elements 126 could be changed to match a color associated with an advertising campaign or in accordance with a color scheme that is associated with the merchant.

The voice command system 128 can include any automated voice controlled system that allows a user to interact with the vehicle controller 112 using words, phrases, or natural language input. For example, the voice command system 128 can be used to instruct a user in utilizing the features of the vehicle 104. This voice command system 128 can be adapted through the ambience profile to guide users in their shopping experience. For example, the ambience profile includes a chatbot or other similar functionality that engages in small talk with the user or utilizes a script in order to walk the user through completing a purchase. This script is generally referred to as a voice assist protocol. The merchant can configure how the voice assist protocol will engage with a customer within the ambience profile. In some embodiments, this customization of the voice assist protocol is performed based on the preference profile for the user.

According to some embodiments, the vehicle 104 comprises seat sensors and/or components 138 are integrated into one or more of the seats of the vehicle 104. Example seat sensors could include temperature or heartrate sensors that gather biometric data from a user in an enable seat. The components of the seat could include any one or more of a heating, cooling, or other similar ventilation assembly, a massage or vibration assembly, a positioning assembly that allows for selective positioning of seat sections.

The climate control system 130 allows a user to select a temperature within the vehicle 104 as well as control other aspects of climate such as seat heating or cooling. In some embodiments, the climate control system 130 can be controlled through use of the ambience profile and/or the preference profile to increase or decrease temperature or airspeed within the vehicle. In one example use case, the merchant provides vacation services, and the ambience profile includes instructions that cause the entertainment or infotainment system 124 to play a video of a beach scene while the climate control system 130 causes the temperature within the vehicle to be set at 82 degrees, and an airspeed is set to high to mimic a beach environment. The vehicle controller 112 can also cause the climate control system 130 to activate heaters in the seat where the user is located using the seat sensors and/or components 138. As discussed below, the ambience profile can also include instructions that cause a scent dispenser within the vehicle to dispense a tropical scent. These facets collectively create an immersive experience for users, enticing them into purchasing a vacation.

As noted above, the scent dispenser 132 includes a device that is configured to output scents that are associated with an ambience profile. The scent can be specified in the ambience profile or could include a scent favored by the user, as established in the preference profile for the user. These various subsystems of the micro-environment assembly 114 can be controlled to function collectively or individually to provide an immersive experience to a user during a shopping experience. To be sure, this immersive experience can be triggered when the user has engaged in a shopping experience on his/her mobile device or wearable 122. Alternatively, the user can be enticed into engaging in a shopping experience by first activating an ambience profile and then subsequently fine tuning the experience based on the preference profile.

In one example embodiment, the service provider 102 can provide a preference profile to the vehicle controller 112 when a user books a ride-share trip. This embodiment assumes that the vehicle 104 is used for providing ride-sharing services. The preference indicates that the user typically orders food from a particular merchant for dinner on this particular day of the week. To entice the user to order food from the merchant, the service provider 102 obtains an ambience profile for the merchant and provides the same to the vehicle controller 112. The vehicle controller 112 can activate the scent dispenser 132 of the micro-environment assembly 114 to output scents that are associated with food frequently ordered by the user from the merchant. If the user completes a transaction and orders food from the merchant, the service provider 102 can coordinate delivery of the food to a destination or home address indicated in the ride request. Again, this is merely an example of a use case of the present disclosure and is not intended to be limiting.

During an immersive experience, the vehicle controller 112 can be configured to track user feedback or behaviors. That is, when the vehicle controller 112 is executing the ambience profile and/or the preference profile, the vehicle controller 112 can track user feedback or behaviors. This may include tracking how the user responds to any of the sensory stimuli presented. For example, if the user activates the windows after a scent is dispensed, the service provider 102 can track this action and infer that the user did not like the scent. The vehicle controller 112 can also track the browser activity of the user on his/her mobile device or wearable 122. For example, if the user clicked out of a website or away from a product featured in a shopping experience, the service provider 102 can infer that the user has no interest in the product. In addition, the vehicle controller 112 can be configured to track the pickup and drop off locations of the user. For example, based on the user preferences and pickup and drop-off locations of the user, the service provider 102 may instruct the vehicle controller 112 may present the user with targeted advertisements. In one example embodiment, the user may be heading to a Nike outlet at their drop-off location. The vehicle controller 112 can present the user with Nike advertisements and/or also get goods ready at the Nike store that correspond to the user's preferences. Furthermore, advertisements (scent, lights in vehicle) can also be used to give user a discount on their ride. Again, this would be based on the user preferences (e.g., allergic to leather smell, etc.).

In addition to tracking user behaviors, the vehicle controller 112 can also activate the one or more biometric sensors 134. In some embodiments, the one or more biometric sensors 134 are associated with a seat of the vehicle (specifically the seat sensors and/or components 138). The one or more biometric sensors 134 can collect biometric data such as heart rate, pulse, body temperature, or other similar biometric data. The vehicle controller 112 can provide this biometric data to the service provider 102. The service provider 102 can be configured to determine at least one of a mood, a heart rate, or a comfort level for the user based on the biometric feedback. For example, if the user's pulse elevates during an immersive experience, it can be inferred that the user is upset or excited. This biometric feedback can be tracked and associated with an ambience profile that was used to create the immersive experience. The service provider 102 can update the preference profile for the user based on any of the tracked data or feedback that was obtained by the vehicle controller 112. This can be facilitated using the preference assimilation service 110 of the service provider 102 described above. The feedback can also be provided to the merchant by the service provider 102. The merchant can use this feedback to improve its ambience profiles.

In some embodiments, rather than tracking operations performed on the mobile device or wearable 122, the vehicle 104 can comprise a vehicle shopping platform 136. The vehicle shopping platform 136 is generally described as a human machine interface such as a kiosk or display terminal. The vehicle shopping platform 136 is accessible to riders within the vehicle 104 and provides in-vehicle shopping experiences in combination with the micro-environment assembly 114.

According to some embodiments, the vehicle 104 can also comprise an IoT device interface 140 that can be configured to allow other Internet-of-Things (IoT) devices to interface with the platform providing the in-vehicle shopping experience. The IoT device interface 140 could include, for example, a USB port that allows a third-party IoT device (IoT Device 142) to be connected to the micro-environment assembly 114. The type of interface or interfaces included in the IoT device interface 140 may vary depending upon the IoT devices that may be used within the micro-environment assembly 114. In one embodiment, merchants can distribute their own IoT devices, such as scent dispensers that are configured to dispense scents that are uniquely configured for use with the ambiance profiles offered by the merchant. The IoT device 142 would have a corresponding or complementary interface that allows the IoT device 142 to mate with the IoT device interface 140. While a scent dispenser has been described as a potential example IoT device 142, other IoT devices can also be utilized to provide any one or combination of sensory output such as audio, visual, tactile, and the like.

Illustrative Methods and Operations

Figure 2:
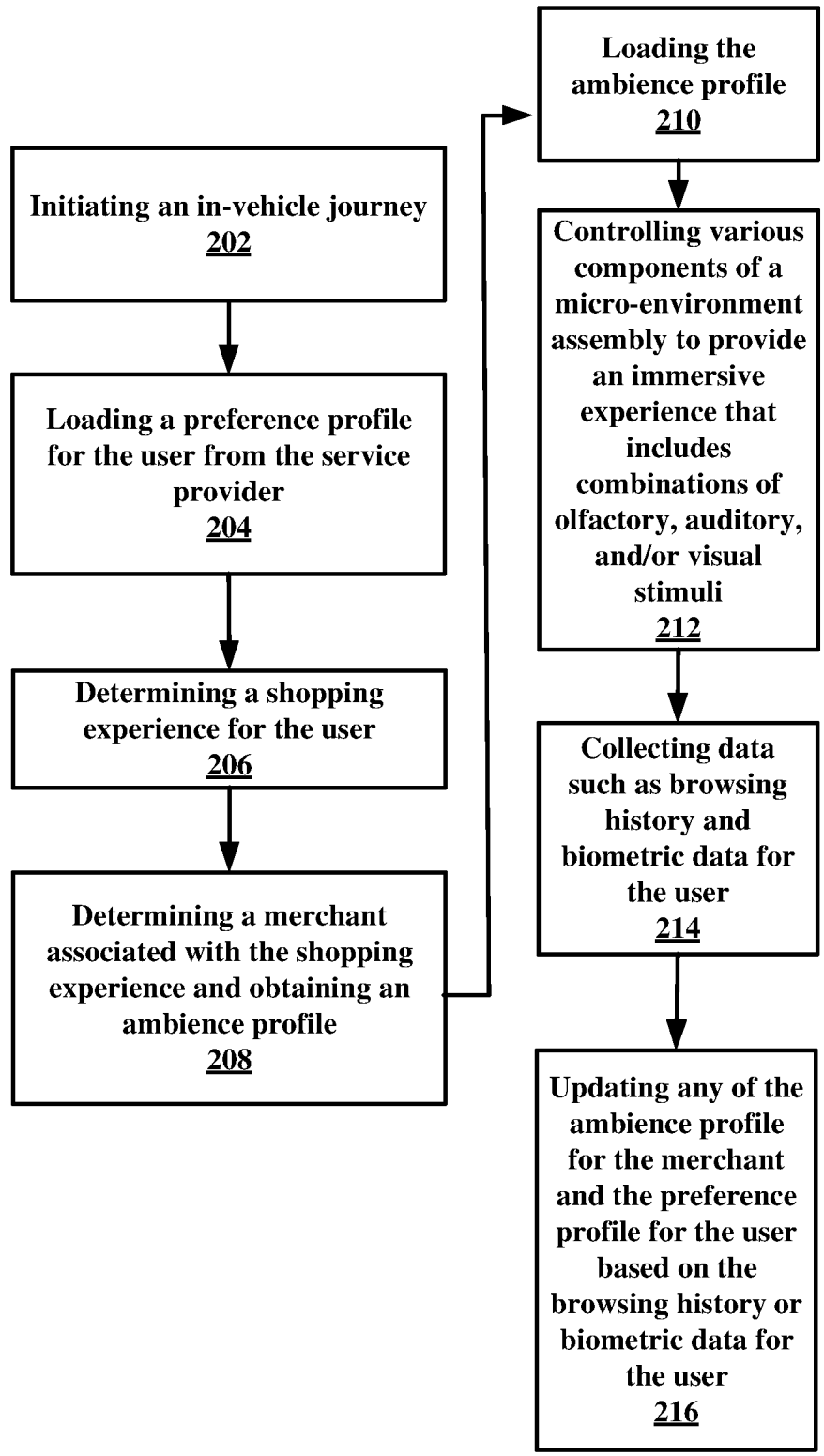
FIG. 2 is a flowchart of a method of the present disclosure that is generally directed to an example use case where aspects of the present disclosure are implemented.

The following descriptions provide additional details on function and methodological aspects of the present disclosure provided through the architectures and/or systems disclosed above. FIG. 2 is a flowchart of an example method of the present disclosure. The method involves providing an immersive shopping experience for a user. For context, the user is participating in a ride-sharing service. A vehicle providing the ride-sharing service is enabled with a vehicle controller and a micro-environment assembly in accordance with the present disclosure. The immersive shopping experience and the ride-sharing service are mediated through a service provider.

In some embodiments, the method includes a step 202 of initiating an in-vehicle journey. This can include a user entering a ride-sharing vehicle in order to be transported from a pickup location to a destination. The method includes a step 204 of loading a preference profile for the user from the service provider. The preference profile could include information gathered during previous vehicle interactions. In some embodiments, the method includes a step 206 of determining a shopping experience for the user. As noted above, this can include tracking browser activity on a mobile device or wearable connected to the WiFi of the vehicle, as well as a pickup and/or drop off location. In another embodiment this can include tracking activity on a vehicle shopping platform. The method includes a step 208 of determining a merchant associated with the shopping experience and obtaining an ambience profile. For example, the user may be searching for shoes provided by a particular retailer. The service provider can identify a domain name and product name identified in the browser activity.

In some embodiments, the method includes a step 210 of loading the ambience profile. The loading of the ambience profile could result in controlling the voice command system of the vehicle to execute a voice assist protocol to engage with the user. This can occur as the user is browsing products on the merchant's website. The method can also include a step 212 of controlling various components of a micro-environment assembly to provide an immersive experience that includes combinations of olfactory, auditory, and/or visual stimuli.

While shopping, the method can include a step 214 of collecting data such as browsing history and biometric data for the user. This feedback is uploaded to the service provider for analysis and use. For example, the feedback is provided as input into a machine learning function of the service provider for ambience profile creation or improvement. The feedback can also be used to dynamically update an ambience profile or a preference profile for the user. For example, the user might indicate that the product being offered is of no interest to the user. This negative feedback can be used to improve both the ambience profile for the merchant and the preference profile for the user. In sum, the method includes a step 216 of updating any of the ambience profile for the merchant and the preference profile for the user based on the browsing history or biometric data for the user.

Figure 3:
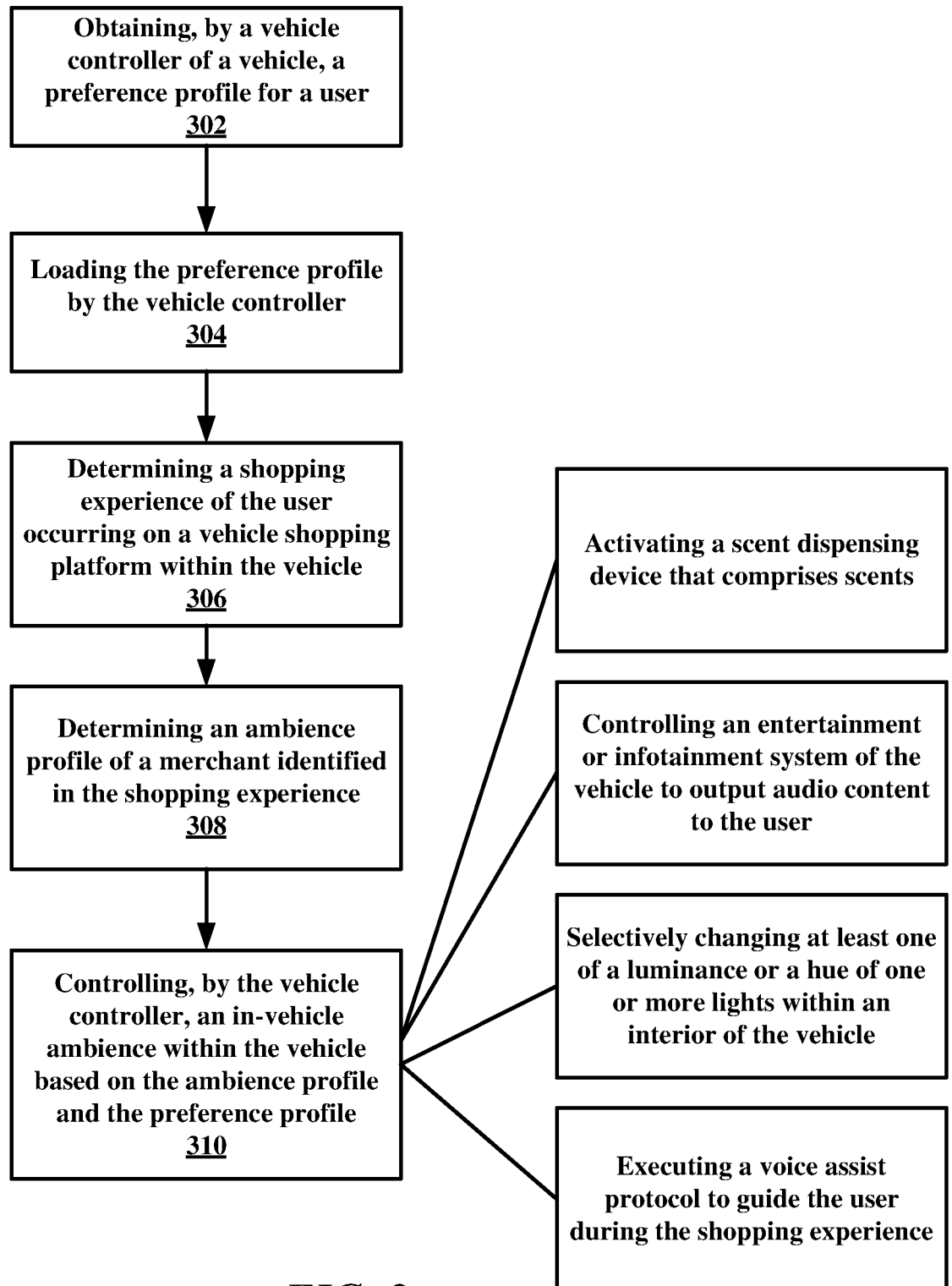
FIG. 3 is a flowchart of an example method of the present disclosure.

FIG. 3 is a flowchart of another example method of the present disclosure. The method includes a step 302 of obtaining, by a vehicle controller of a vehicle, a preference profile for a user. This step can occur when a user enters a vehicle or when the user requests a ride-sharing service. The user can be linked to his/her preference profile using any unique identifier such as an email address. The method further includes a step 304 of loading the preference profile by the vehicle controller. Next, the method can include a step 306 of determining a shopping experience of the user occurring on a vehicle shopping platform within the vehicle. For example, the user can browse on the vehicle shopping platform or on his/her mobile device for goods or items. Alternatively, the user can be presented with an advertising campaign during the ride. Regardless, the method includes a step 308 of determining an ambience profile of a merchant identified in the shopping experience. The method also includes a step 310 of controlling, by the vehicle controller, an in-vehicle ambience within the vehicle based on the ambience profile and the preference profile. As noted above, this includes controlling aspects of a micro-environment system of the vehicle to produce a unique combination of stimuli. This could include activating a scent dispensing device that comprises scents. The scents selected are specified in the ambience profile. In other embodiments, the step 310 includes controlling an entertainment or infotainment system of the vehicle to output audio content to the user.

According to some embodiments, the step 310 can include selectively changing at least one of a luminance or a hue of one or more lights within an interior of the vehicle. In yet other embodiments, the step 310 can include executing a voice assist protocol to guide the user during the shopping experience. To be sure, the voice assist protocol is a part of the ambience profile.

Figure 4:
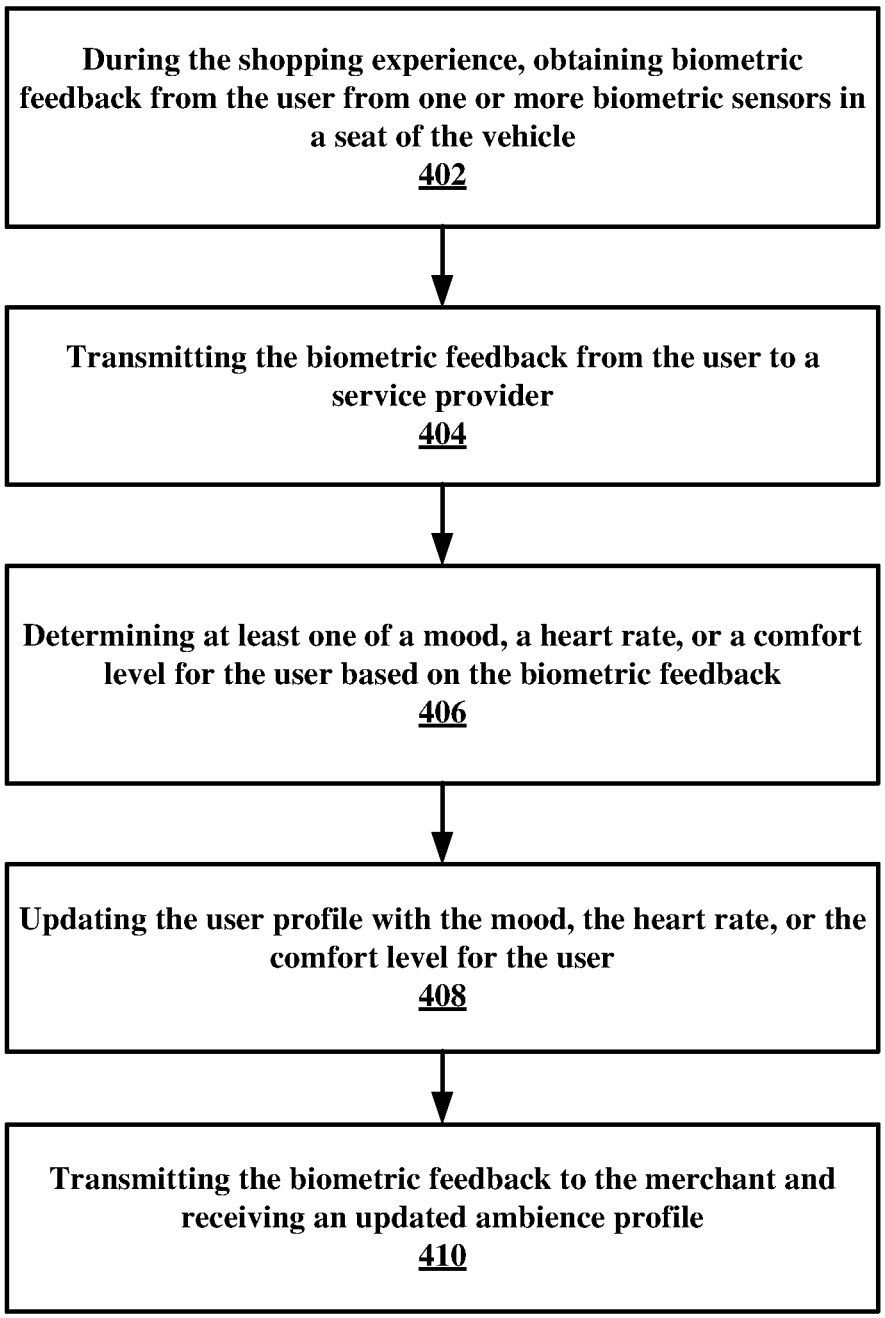
FIG. 4 is a flowchart of another example method of the present disclosure related to using biometric feedback to improve preference and/or ambience profiles.

FIG. 4 is another flowchart of an example method that can be used in combination with the method of FIG. 3. The method can include a step 402 of during the shopping experience, obtaining biometric feedback from the user from one or more biometric sensors in a seat of the vehicle. The method can include a step 404 of transmitting the biometric feedback from the user to a service provider. The method can also include a step 406 of determining at least one of a mood, a heart rate, or a comfort level for the user based on the biometric feedback. It will be understood that mood and comfort level are inferred states for the user based on the biometric feedback. For example, heart rate and body temperature can be indicative of either mood and/or comfort level. Also, pressure sensors in the seats can detect user movement, which might also be indicative of mood and/or comfort level.

According to some embodiments, the method can include a step 408 of updating the user profile with the mood, the heart rate, or the comfort level for the user. The method can also include a step 410 of transmitting the biometric feedback to the merchant. The merchant can utilize this biometric feedback (sometimes in combination with the preference profile) to improve its ambience profiles and provide an updated ambience profile.

EXAMPLE EMBODIMENTS

In some instances, the following examples may be implemented together or separately by the systems and methods described herein.

Example 1 may include a method, comprising: obtaining, by a vehicle controller of a vehicle, a preference profile for a user; loading the preference profile by the vehicle controller; determining a shopping experience of the user occurring on a vehicle shopping platform within the vehicle; determining an ambience profile of a merchant identified in the shopping experience; and controlling, by the vehicle controller, an in-vehicle ambience within the vehicle based on the ambience profile and the preference profile.

Example 2 may include the method according to example 1, wherein controlling, by the vehicle controller, the in-vehicle ambience within the vehicle based on the ambience profile and the preference profile further comprises activating a scent dispensing device that comprises scents.

Example 3 may include the method according to example 1 and/or some other example herein, wherein controlling, by the vehicle controller, the in-vehicle ambience within the vehicle based on the ambience profile and the preference profile further comprises controlling an entertainment or infotainment system of the vehicle to output audio content to the user.

Example 4 may include the method according to example 1 and/or some other example herein, wherein controlling, by the vehicle controller, the in-vehicle ambience within the vehicle based on the ambience profile and the preference profile further comprises selectively changing at least one of a luminance or a hue of one or more lighting elements within an interior of the vehicle.

Example 5 may include the method according to example 1 and/or some other example herein, further comprising executing a voice assist protocol to guide the user during the shopping experience, the voice assist protocol being a part of the ambience profile.

Example 6 may include the method according to example 1 and/or some other example herein, further comprising: during the shopping experience, obtaining biometric feedback from the user from one or more biometric sensors in a seat of the vehicle; determining at least one of a mood, a heart rate, or a comfort level for the user based on the biometric feedback; and updating the user profile with the mood, the heart rate, or the comfort level for the user.

Example 7 may include a vehicle, comprising: a micro-environment assembly configured to selectively adjust an ambience within a vehicle by providing any combination of one or more of visual, auditory, or olfactory output; and a vehicle controller comprising a processor and a memory, the processor being configured to execute instructions stored in the memory to: obtain a preference profile for a user; load the preference profile by the vehicle controller; determine a shopping experience of the user occurring on a vehicle shopping platform within the vehicle; determine an ambience profile of a merchant identified in the shopping experience; and control the micro-environment assembly to selectively adjust the ambience within the vehicle based on the ambience profile and the preference profile to provide the user with an immersive experience.

Example 8 may include the vehicle according to example 7, wherein the micro-environment assembly comprises a scent dispenser that outputs scented compounds in accordance with at least one of the ambience profile or the preference profile.

Example 9 may include the vehicle according to example 7 and/or some other example herein, wherein the vehicle controller is further configured to execute instructions stored in the memory to cause an entertainment or infotainment system of the vehicle to output audio content to the user in accordance with at least one of the ambience profile or the preference profile.

Example 10 may include the vehicle according to example 7 and/or some other example herein, further comprising one or more lighting elements within an interior of the vehicle, wherein the vehicle controller is further configured to execute instructions stored in the memory to selectively change at least one of a luminance or a hue of the one or more lighting elements in accordance with at least one of the ambience profile or the preference profile.

Example 11 may include the vehicle according to example 7 and/or some other example herein, further comprising a voice command system, wherein the vehicle controller is further configured to execute instructions stored in the memory to implement a voice assist protocol on the voice command system to guide the user during the shopping experience.

Example 12 may include the vehicle according to example 11 and/or some other example herein, wherein the voice assist protocol is a part of the ambience profile, the voice assist protocol comprising an interactive chat feature that provides question and answer engagement with the user.

Example 13 may include the vehicle according to example 7 and/or some other example herein, wherein the vehicle controller is further configured to execute instructions stored in the memory to cause a climate control system of the vehicle to increase or decrease temperature or airspeed within the vehicle.

Example 14 may include the vehicle according to example 7 and/or some other example herein, further comprising one or more biometric sensors within a seat of the vehicle, wherein the vehicle controller is further configured to execute instructions stored in the memory to: during the shopping experience, obtain biometric feedback from the user from the one or more biometric sensors; determine at least one of a mood, a heart rate, or a comfort level for the user based on the biometric feedback; and update the user profile with the mood, the heart rate, or the comfort level for the user.

Example 15 may include a system, comprising: a service provider that: generates and maintains preference profiles of users; and obtains ambience profiles from third-party entities; and a vehicle comprising: a micro-environment assembly configured to selectively adjust an ambience within a vehicle by providing any combination of one or more of visual, auditory, or olfactory output; and a vehicle controller comprising a processor and a memory, the processor being configured to execute instructions stored in the memory to: obtain a preference profile for a user from the service provider; load the preference profile by the vehicle controller; determine a shopping experience of the user occurring on a vehicle shopping platform within the vehicle; determine an ambience profile of a merchant identified in the shopping experience; load the ambience profile by the vehicle controller; and control the micro-environment assembly to selectively adjust the ambience within the vehicle based on the ambience profile and the preference profile.

Example 16 may include the system according to example 15, further comprising one or more biometric sensors within a seat of the vehicle, wherein the vehicle controller is further configured to execute instructions stored in the memory to: during the shopping experience, obtain biometric feedback from the user from the one or more biometric sensors; determine at least one of a mood, a heart rate, or a comfort level for the user based on the biometric feedback; and update the user profile with the mood, the heart rate, or the comfort level for the user.

Example 17 may include the system according to example 15 and/or some other example herein, wherein the microenvironment assembly comprises a scent dispenser that outputs scented compounds in accordance with at least one of the ambience profile or the preference profile.

Example 18 may include the system according to example 15 and/or some other example herein, wherein the vehicle controller is further configured to execute instructions stored in the memory to cause an entertainment or infotainment system of the vehicle to output audio content to the user in accordance with at least one of the ambience profile or the preference profile.

Example 19 may include the system according to example 15 and/or some other example herein, further comprising one or more lighting elements within an interior of the vehicle, wherein the vehicle controller is further configured to execute instructions stored in the memory to selectively change at least one of a luminance or a hue of the one or more lighting elements in accordance with at least one of the ambience profile or the preference profile.

Example 20 may include the system according to example 15 and/or some other example herein, further comprising a voice command system, wherein the vehicle controller is further configured to execute instructions stored in the memory to implement a voice assist protocol on the voice command system to guide the user during the shopping experience.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, one skilled in the art will recognize such feature, structure, or characteristic in connection with other embodiments whether or not explicitly described.

Implementations of the systems, apparatuses, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that stores computer-executable instructions is computer storage media (devices). Computer-readable media that carries computer-executable instructions is transmission media. Thus, by way of example, and not limitation, implementations of the present disclosure can comprise at least two distinctly different kinds of computer-readable media: computer storage media (devices) and transmission media.

Computer storage media (devices) includes RAM, ROM, EEPROM, CD-ROM, solid state drives (SSDs) (e.g., based on RAM), flash memory, phase-change memory (PCM), other types of memory, other optical disk storage, magnetic disk storage or other magnetic storage devices, or any other medium which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or any combination of hardwired or wireless) to a computer, the computer properly views the connection as a transmission medium. Transmission media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the present disclosure may be practiced in network computing environments with many types of computer system configurations, including in-dash vehicle computers, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by any combination of hardwired and wireless data links) through a network, both perform tasks. In a distributed system environment, program modules may be located in both the local and remote memory storage devices.

Further, where appropriate, the functions described herein can be performed in one or more of hardware, software, firmware, digital components, or analog components. For example, one or more application specific integrated circuits (ASICs) can be programmed to carry out one or more of the systems and procedures described herein. Certain terms are used throughout the description and claims refer to particular system components. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein for purposes of illustration and are not intended to be limiting. Embodiments of the present disclosure may be implemented in further types of devices, as would be known to persons skilled in the relevant art(s).

At least some embodiments of the present disclosure have been directed to computer program products comprising such logic (e.g., in the form of software) stored on any computer-usable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Further, it should be noted that any or all of the aforementioned alternate implementations may be used in any combination desired to form additional hybrid implementations of the present disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A method, comprising:
   obtaining, by a vehicle controller of a vehicle, a preference profile for a user;
   loading the preference profile by the vehicle controller;
   determining a shopping experience of the user occurring on a vehicle shopping platform within the vehicle;
   determining an ambience profile of a merchant identified in the shopping experience; and
   controlling, by the vehicle controller, an in-vehicle ambience within the vehicle based on the ambience profile and the preference profile.

2. The method according to claim 1, wherein controlling, by the vehicle controller, the in-vehicle ambience within the vehicle based on the ambience profile and the preference profile further comprises activating a scent dispensing device that comprises scents.

3. The method according to claim 1, wherein controlling, by the vehicle controller, the in-vehicle ambience within the vehicle based on the ambience profile and the preference profile further comprises controlling an entertainment or infotainment system of the vehicle to output audio content to the user.

4. The method according to claim 1, wherein controlling, by the vehicle controller, the in-vehicle ambience within the vehicle based on the ambience profile and the preference profile further comprises selectively changing at least one of a luminance or a hue of one or more lighting elements within an interior of the vehicle.

5. The method according to claim 1, further comprising executing a voice assist protocol to guide the user during the shopping experience, the voice assist protocol being a part of the ambience profile.

6. The method according to claim 1, further comprising:
   during the shopping experience, obtaining biometric feedback from the user from one or more biometric sensors in a seat of the vehicle;
   determining at least one of a mood, a heart rate, or a comfort level for the user based on the biometric feedback; and
   updating the user profile with the mood, the heart rate, or the comfort level for the user.

7. A vehicle, comprising:
   a micro-environment assembly configured to selectively adjust an ambience within a vehicle by providing any combination of one or more of visual, auditory, or olfactory output; and
   a vehicle controller comprising a processor and a memory, the processor being configured to execute instructions stored in the memory to:
   obtain a preference profile for a user;
   load the preference profile by the vehicle controller;
   determine a shopping experience of the user occurring on a vehicle shopping platform within the vehicle;
   determine an ambience profile of a merchant identified in the shopping experience; and
   control the micro-environment assembly to selectively adjust the ambience within the vehicle based on the ambience profile and the preference profile to provide the user with an immersive experience.

8. The vehicle according to claim 7, wherein the micro-environment assembly comprises a scent dispenser that outputs scented compounds in accordance with at least one of the ambience profile or the preference profile.

9. The vehicle according to claim 7, wherein the vehicle controller is further configured to execute instructions stored in the memory to cause an entertainment or infotainment system of the vehicle to output audio content to the user in accordance with at least one of the ambience profile or the preference profile.

10. The vehicle according to claim 7, further comprising one or more lighting elements within an interior of the vehicle, wherein the vehicle controller is further configured to execute instructions stored in the memory to selectively change at least one of a luminance or a hue of the one or more lighting elements in accordance with at least one of the ambience profile or the preference profile.

11. The vehicle according to claim 7, further comprising a voice command system, wherein the vehicle controller is further configured to execute instructions stored in the memory to implement a voice assist protocol on the voice command system to guide the user during the shopping experience.

12. The vehicle according to claim 11, wherein the voice assist protocol is a part of the ambience profile, the voice assist protocol comprising an interactive chat feature that provides question and answer engagement with the user.

13. The vehicle according to claim 7, wherein the vehicle controller is further configured to execute instructions stored in the memory to cause a climate control system of the vehicle to increase or decrease temperature or airspeed within the vehicle.

14. The vehicle according to claim 7, further comprising one or more biometric sensors within a seat of the vehicle, wherein the vehicle controller is further configured to execute instructions stored in the memory to:
- during the shopping experience, obtain biometric feedback from the user from the one or more biometric sensors;
- determine at least one of a mood, a heart rate, or a comfort level for the user based on the biometric feedback; and
- update the user profile with the mood, the heart rate, or the comfort level for the user.

15. A system, comprising:
a service provider that:
- generates and maintains preference profiles of users; and
- obtains ambience profiles from third-party entities; and a vehicle comprising:
- a micro-environment assembly configured to selectively adjust an ambience within a vehicle by providing any combination of one or more of visual, auditory, or olfactory output; and
- a vehicle controller comprising a processor and a memory, the processor being configured to execute instructions stored in the memory to:
  - obtain a preference profile for a user from the service provider;
  - load the preference profile by the vehicle controller;
  - determine a shopping experience of the user occurring on a vehicle shopping platform within the vehicle;
  - determine an ambience profile of a merchant identified in the shopping experience;
  - load the ambience profile by the vehicle controller; and
  - control the micro-environment assembly to selectively adjust the ambience within the vehicle based on the ambience profile and the preference profile.

16. The system according to claim 15, further comprising one or more biometric sensors within a seat of the vehicle, wherein the vehicle controller is further configured to execute instructions stored in the memory to:
- during the shopping experience, obtain biometric feedback from the user from the one or more biometric sensors;
- determine at least one of a mood, a heart rate, or a comfort level for the user based on the biometric feedback; and
- update the user profile with the mood, the heart rate, or the comfort level for the user.

17. The system according to claim 15, wherein the micro-environment assembly comprises a scent dispenser that outputs scented compounds in accordance with at least one of the ambience profile or the preference profile.

18. The system according to claim 15, wherein the vehicle controller is further configured to execute instructions stored in the memory to cause an entertainment or infotainment system of the vehicle to output audio content to the user in accordance with at least one of the ambience profile or the preference profile.

19. The system according to claim 15, further comprising one or more lighting elements within an interior of the vehicle, wherein the vehicle controller is further configured to execute instructions stored in the memory to selectively change at least one of a luminance or a hue of the one or more lighting elements in accordance with at least one of the ambience profile or the preference profile.

20. The system according to claim 15, further comprising a voice command system, wherein the vehicle controller is further configured to execute instructions stored in the memory to implement a voice assist protocol on the voice command system to guide the user during the shopping experience.

* * * * *